(12) United States Patent
Tanaka et al.

(10) Patent No.: US 9,029,593 B2
(45) Date of Patent: May 12, 2015

(54) METHOD FOR MANUFACTURING SPILANTHOL AND INTERMEDIATE MANUFACTURING PRODUCT THEREFOR

(75) Inventors: Shigeru Tanaka, Hiratsuka (JP); Kenya Ishida, Hiratsuka (JP); Kenji Yagi, Hiratsuka (JP); Hideo Ujihara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 793 days.

(21) Appl. No.: 13/383,547

(22) PCT Filed: Jul. 14, 2010

(86) PCT No.: PCT/JP2010/061912
§ 371 (c)(1),
(2), (4) Date: Jan. 11, 2012

(87) PCT Pub. No.: WO2011/007807
PCT Pub. Date: Jan. 20, 2011

(65) Prior Publication Data
US 2012/0116116 A1 May 10, 2012

(30) Foreign Application Priority Data
Jul. 14, 2009 (JP) ................................ 2009-165530

(51) Int. Cl.
| C07C 231/12 | (2006.01) |
| C07C 235/28 | (2006.01) |
| A61K 31/16 | (2006.01) |
| A61K 8/42 | (2006.01) |
| A61Q 13/00 | (2006.01) |
| C07C 233/09 | (2006.01) |
| A23L 2/56 | (2006.01) |
| A23L 1/226 | (2006.01) |
| C11B 9/00 | (2006.01) |

(52) U.S. Cl.
CPC . *A61K 31/16* (2013.01); *A61K 8/42* (2013.01); *A61Q 13/00* (2013.01); *C07C 231/12* (2013.01); *C07C 233/09* (2013.01); *C07C 235/28* (2013.01); *A23L 2/56* (2013.01); *A23L 1/22614* (2013.01); *C11B 9/0007* (2013.01)

(58) Field of Classification Search
CPC .. C07C 231/12; C07C 233/09; C07C 235/28; A61K 8/42; A61K 31/16; A61Q 13/00; A23L 2/56; A23L 1/22614; C11B 9/0007
See application file for complete search history.

(56) References Cited

U.S. PATENT DOCUMENTS

| 7,312,339 B2 * | 12/2007 | McAlpine et al. ............ 548/236 |
| 8,217,192 B2 * | 7/2012 | Tanaka et al. ................. 554/45 |
| 2008/0050500 A1 | 2/2008 | Muranishi et al. |
| 2008/0069912 A1 | 3/2008 | Demarne et al. |
| 2009/0124701 A1 | 5/2009 | Langer et al. |
| 2010/0184863 A1 | 7/2010 | Lombardo et al. |

FOREIGN PATENT DOCUMENTS

| JP | 07-090294 A | 4/1995 |
| JP | 2006-296356 A | 11/2006 |
| JP | 2006-296357 A | 11/2006 |
| JP | 2007-517842 A | 7/2007 |
| WO | WO 2006/068065 A1 | 6/2006 |
| WO | WO 2006/087991 A | 8/2006 |
| WO | WO 2009/091040 A1 | 7/2009 |

OTHER PUBLICATIONS

Harding et al., "Syntheses of Isotopically Labelled L-α-amino Acids with an Asymmetric Centre at C-3," J. Chem. Soc., Perkin Trans., 2000, pp. 3406-3416.
European Patent Office, European Search Report issued in corresponding EP Application No. 10799865.0, dated Nov. 22, 2012.
L. Crombie, et al., "Synthesis of N-isoButyldeca-trans-2, cis-6, trans-8- and -trans-2, cis-6, cis-8-trienamide", Chemistry and Industry, Jun. 2, 1962, pp. 983-984.
Martin Jacobson, "Constituents of Heliopsis Species. IV. The Total Synthesis of trans-Affinin", Total Synthesis of trans-Affinin, J. Am. Chem., Soc., May 5, 1955, pp. 2461-2463.
Martin Jacobson, "Naturally Occurring Insecticides", The Unsaturated Isobutylamides, 1971, pp. 137-157.
Yasuhiro Takashima, et al., "Nitrogen Compounds", Koryo, 1985, vol. 145, pp. 121-134.
Yoshihiko Ikeda, et al., "Facile Routes to Natural Acyclic Polyenes Synthesis of Spilanthol and Trail Pheromone for Termite", Tetrahedron Letters, 1984, pp. 5177-5180, vol. 25, No. 45.
Yoshihiko Ikeda, et al., "Stereoselective Synthesis of 1,4-Disubstituted 1,3-Diene from Aldehyde Using Organotitanium Reagent", Tetrahedron, 1987, pp. 731-741, vol. 43, No. 4.
Zhong Wang, et al., "Efficient Preparation of Functionalized (E,Z) Dienes Using Acetylene as the Building Block", J. Org. Chem., 1998, pp. 3806-3807, vol. 63, No. 12.

* cited by examiner

Primary Examiner — Joseph Kosack
Assistant Examiner — Amanda L Aguirre
(74) Attorney, Agent, or Firm — Sughrue Mion, PLLC

(57) ABSTRACT

Provided is an amide ester that is useful as an intermediate manufacturing product for an aroma compound such as spilanthol or the like. Also provided is a spilanthol manufacturing method using said amide ester. High-purity spilanthol can be manufactured by reacting an amide ester represented by general formula (1) with a basic compound.

(1)

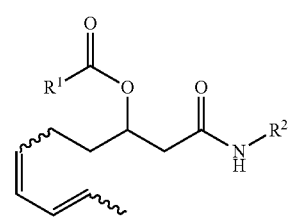

(In the formula, $R^1$ represents a C1-6 alkyl group or a phenyl group that may be substituted with a $C_{1-4}$ alkyl group, a $C_{1-4}$ alkoxy group, or a halogen atom; $R^2$ represents a $C_{1-8}$ hydrocarbon group; and the wavy lines represent cis configurations, trans configurations, or a mixture of the two configurations.)

5 Claims, No Drawings

METHOD FOR MANUFACTURING SPILANTHOL AND INTERMEDIATE MANUFACTURING PRODUCT THEREFOR

CROSS REFERENCE TO RELATED APPLICATIONS

This application is a National Stage of International Application No. PCT/JP2010/061912 filed Jul. 14, 2010, which claims priority from Japanese Patent Application No. 2009-165530, filed Jul. 14, 2009, the contents of all of which are incorporated herein by reference in their entirety.

TECHNICAL FIELD

The present invention relates to a manufacturing method enabling manufacturing of spilanthol which is useful as flavors and fragrances in an aromatically favorable state, and a novel intermediate used in the method.

BACKGROUND ART

Spilanthol (N-isobutyl-2,6,8-decatrienamide) is known to cause a smarting or numbing stimulus and/or a piercing stimulative feeling, and used as spices and/or herb spices in foods and beverages. Particularly, a (2E,6Z,8E) isomer is known to be a main component of *Spilanthes oleracea*, and as an effective component having strong numbing and astringent actions. The (2E,6Z,8E) isomer is useful as a sense stimulus component in a wide range of products such as foods, beverages, fragrances and cosmetic. Meanwhile, as a method of obtaining spilanthol there is known a method, for example, in which spilanthol is derived from naturally-occurring products such as by extraction from *Spilanthes oleracea*. In addition, Non Patent Literatures 1, 2 and 3, and so forth disclose methods of synthesizing spilanthol. However, such methods are not considered as industrially-applicable production methods. Incidentally, Patent Literature 1 discloses several industrially-applicable production methods.

CITATION LIST

Patent Literature

Patent Literature 1: WO2009/091040 A1

Non Patent Literatures

Non Patent Literature 1: J. Am. Chem. Soc., 2461-2463, (1955)
Non Patent Literature 2: Naturally Occurring Insecticides, 149-156 (1971)
Non Patent Literature 3: Tetrahedron, 731-741 (1987)

SUMMARY OF INVENTION

Technical Problem

An object of the present invention is to provide a method for manufacturing aromatically favorable spilanthol in high yield, and a novel intermediate used in the method.

Solution to Problem

The present inventors have earnestly studied to achieve the above-described object. As a result, the inventors have found out that by using a novel amide ester as an intermediate, high-purity, aromatically favorable spilanthol is obtained in high yield.

In other words, the present invention includes the following contents.

[1] An amide ester represented by the following general formula (1):

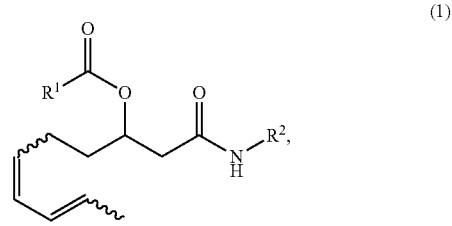

where $R^1$ represents an alkyl group having 1 to 6 carbon atoms;
and a phenyl group may have a substituent selected from the group consisting of alkyl groups having 1 to 4 carbon atoms, alkoxy groups having 1 to 4 carbon atoms and a halogen atom, $R^2$ represents a hydrocarbon group having 1 to 8 carbon atoms, and each wavy line represents a cis configuration, a trans configuration, or a mixture of the two configurations.

[2] The amide ester according to [1], in which $R^1$ is an alkyl group having 1 to 4 carbon atoms.
[3] The amide ester according to [2], in which $R^1$ is a methyl group.
[4] The amide ester according to any one of [1] to [3], in which $R^2$ is an isobutyl group or a s-butyl group.
[5] A method for producing 2,6,8-decatrienamide, including reacting the amide ester according to any one of [1] to [4] with a basic compound.
[6] A food, beverage, fragrance, cosmetic, or pharmaceutical, including 2,6,8-decatrienamide synthesized by the method according to [5] and having a chemical purity of 80% or more and a content of a 2E,6Z,8E-isomer of 65% or more.

Advantageous Effects of Invention

The present invention provides a novel intermediate useful in manufacturing N-isobutyl-2,6,8-decatrienamide (spilanthol) useful as flavors and fragrances. The use of the intermediate enables manufacturing of high-purity, aromatically favorable spilanthol in high yield.

DESCRIPTION OF EMBODIMENTS

Hereinafter, the present invention will be described in more details.

A compound of the present invention represented by a general formula (1) is an amide ester which can be obtained by the following method.

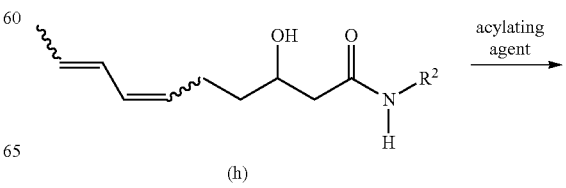

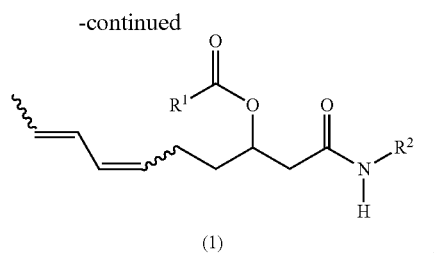

(1)

Examples of an alkyl group having 1 to 6 carbon atoms represented by $R^1$ include a methyl group, an ethyl group, a n-propyl group, an isopropyl group, a n-butyl group, an isobutyl group, a s-butyl group, a t-butyl group, a n-pentyl group, a n-hexyl group, and the like.

Moreover, $R^1$ represents a phenyl group which may be substituted with an alkyl group having 1 to 4 carbon atoms, an alkoxy group having 1 to 4 carbon atoms, or a halogen atom. Examples of the alkyl group include a methyl group, an ethyl group, a n-propyl group, an isopropyl group, a n-butyl group, an isobutyl group, a s-butyl group, and a t-butyl group. Examples of the alkoxy group having 1 to 4 carbon atoms include a methoxy group, an ethoxy group, a n-propoxy group, an isopropoxy group, a n-butoxy group, an isobutoxy group, a s-butoxy group, and a t-butoxy group. Examples of the halogen atom include a fluorine atom, a chlorine atom, and a bromine atom. $R^1$ is preferably an alkyl group having 1 to 4 carbon atoms. Above all, a methyl group is more preferable.

Examples of a hydrocarbon group having 1 to 8 carbon atoms represented by $R^2$ include: linear or branched alkyl groups such as a methyl group, an ethyl group, a n-propyl group, an isopropyl group, a n-butyl group, an isobutyl group, a s-butyl group, a t-butyl group, a pentyl group, a 2-methylbutyl group, and a hexyl group; a phenyl group and alkyl-substituted phenyl groups such as a tolyl group and a xylyl group; and aralkyl groups such as a benzyl group and a phenethyl group. $R^2$ is preferably an isobutyl group or a s-butyl group.

Examples of an acylating agent used herein include acid anhydrides ($R^1COOCOR^1$), acid chlorides ($R^1COCl$), and the like. Examples of $R^1$ include those described above. Specific examples of the acid anhydride include acetic anhydride, propanoic anhydride, butyric anhydride, and the like. Examples of the acid chloride include acetyl chloride, propionyl chloride, pivaloyl chloride, benzoyl chloride, and the like.

Meanwhile, when the compound (h) is subjected to an acylation reaction, it is preferable that a basic compound coexist. Examples of the basic compound used include triethylamine, tributylamine, pyridine, sodium carbonate, sodium hydroxide, potassium hydroxide, and the like. Among these, triethylamine is preferable.

The acylation reaction for the compound (h) can be performed at a temperature of approximately −5° C. to 100° C., preferably 10° C. to 30° C. The reaction period of around approximately 1 hour to 6 hours is sufficient. Examples of a solvent which can be used in the reaction include toluene, hexane, heptane, diethyl ether, and tetrahydrofuran. Among these, toluene is preferable. The amount of the acylating agent used is 1 time to 2 times, preferably 1.05 times to 1.2 times, as large as the compound (h) in terms of mole.

After the reaction is completed, the product can be purified by extraction, distillation, various chromatographies, or the like.

Note that the compound (h) which is the raw material of the amide ester of the compound of the present invention can be produced, for example, by the following method.

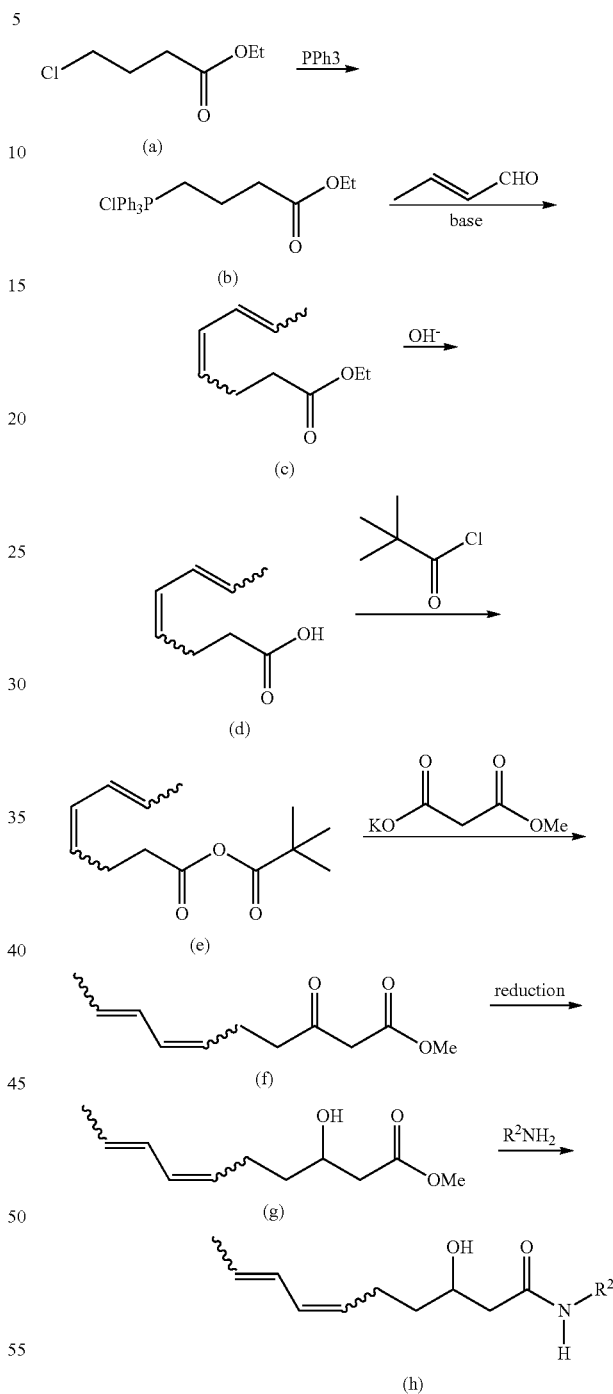

(where each wavy line represents a cis configuration, a trans configuration, or a mixture of the two configurations).

Further, description will be given of a method for producing N-isobutyl-2,6,8-decatrienamide (spilanthol) using a compound (1)-i-Bu which is the amide ester of the present invention represented by the general formula (1) in which $R^2$ is an isobutyl group. The production method is illustrated by the following scheme.

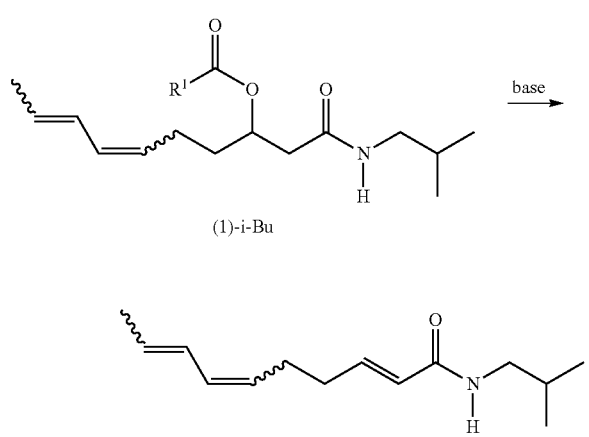

(1)-i-Bu

Examples of a basic compound used herein include amines, alkyllithiums, Grignard reagents, metal hydrides, metal amides, metal alcoholates, and the like. Specific examples of the basic compound include triethylamine, pyridine, 1,8-diazabicyclo[5.4.0]-7-undecene, n-butyllithium, t-butylmagnesium chloride, sodium hydride, lithium amides, lithium diisopropylamide, sodium methoxide, sodium t-butoxide, potassium t-butoxide, and the like. Preferable examples of the basic compound include sodium t-butoxide and potassium t-butoxide.

The reaction can be performed at a temperature of approximately −20° C. to 50° C., preferably 5° C. to 10° C. The reaction period of around approximately 1 hour to 5 hours is sufficient. Examples of a solvent which can be used in the reaction include toluene, heptane, and tetrahydrofuran. Among these, toluene is preferable. The amount of the basic compound used is 1 time to 2 times, preferably 1.05 times to 1.2 times, as large as the compound (1)-i-Bu in terms of moles. After the reaction is completed, the product can be purified by extraction, distillation, various chromatographies, or the like.

The spilanthol obtained in this manner is useful as a flavor additive in foods, beverages, fragrances, cosmetics, pharmaceuticals, and the like, by itself or in combination with sense (the sense of taste, skin sensation, and the like) stimulants such as existing cooling or warming agent, and the like, and more specifically useful as an effective component providing or enhancing cooling sensation, warming sensation, alcohol sensation, carbonation sensation, saliva secretion effect, or the like.

Examples of the above-described existing cooling agent include menthol, menthone, camphor, pulegol, isopulegol, cineol, mentha oil, peppermint oil, spearmint oil, eucalyptus oil, 1-methoxypropane-1,2-diol, N-alkyl-p-menthane-3-carboxamide, N-[(4-cyanomethyl)phenyl]-p-menthanecarboxamide, 3-1-menthoxy-2-methylpropane-1,2-diol, p-menthane-3,8-diol, 2-1-menthoxyethane-1-ol, 3-1-menthoxypropane-1-ol, 1-menthyl lactate, menthone glycerol ketal, N-methyl-2,2-isopropylmethyl-3-methylbutanamide, menthyl glyoxylate, monomenthyl glutarate, monomenthyl succinate, dimenthyl glutarate, dimenthyl succinate, mentha oil, peppermint oil, spearmint and the like. These can be used alone or by optionally blending two or more of them.

Moreover, examples of the warming (hot taste) agent include vanillyl ethyl ether, vanillyl propyl ether, vanillyl butyl ether, vanillin propylene glycol acetal, ethyl vanillin propylene glycol acetal, capsaicin, gingerol, red pepper oil, red pepper oleoresin, ginger oleoresin, nonylic acid vanillylamide, jambu oleoresin, Japanese pepper extract, sanshool-I, sanshool-II, sanshoamide, piper nigrum extract, chavicine, piperine, and the like. These can be used alone or by optionally blending two or more of them.

Note that spilanthol may be directly blended in various products such as foods, beverages, fragrances, cosmetics, and pharmaceuticals. Particularly, it is possible to first blend spilanthol in a flavor or fragrance composition together with the sense stimulant described above, and then blend this flavor or fragrance composition in a product.

Examples of the foods and beverages include drinks such as fruit drinks, fruit wines, milk drinks, carbonated drinks, soft drinks and drink preparations; frozen desserts such as ice creams, sherbets and ice candies; desserts such as jelly and pudding; Western-style confections such as cake, cookie, chocolate and chewing gum; Japanese-style confections such as bean jam bun, sweet beans jelly and uiro; jams; candies; breads; tea drinks or luxury drinks such as green tea, Oolong tea, black tea, persimmon leaf tea, chamomile tea, striped bamboo tea, mulberry tea, Houttuynia cordata tea, Pu-erh tea, Mate tea, Rooibos tea, Gymnema tea, guava tea, coffee and cocoa; soups such as Japanese style soup, Western style soup and Chinese soup; flavor seasonings; various instant drinks and foods; various snack foods; and the like.

Examples of the fragrances and cosmetics include fragrance products such as eau de parfum, eau de toilette and eau de Cologne; basic skin cares such as face washing cream, cleansing cream, cold cream, massage cream, milky lotion, skin toner, beauty lotion, pack and make remover; finishing cosmetics such as foundation, loose face powder, pressed face powder, talcum powder, lipstick, lip cream, rouge, eye liner, mascara, eye shadow and eye pack; hair cosmetics such as pomade, set lotion, hair oil, hair treatment, hair cream, hair tonic, hair liquid, hair spray, revitalizing hair tonic and hair dye; medicinal cosmetics such as suntan cosmetic, antiperspirant, after shaving lotion and jell, permanent wave preparation, medicinal soap, medicinal shampoo and medicinal skin cosmetic; hair care products such as shampoo, rinse, rinse in shampoo, conditioner, treatment and hair pack; body cleaners such as soap, body soap, body shampoo and hand soap; bathing preparations such as bath preparation (bath salt, bath tablet, bath liquid, and the like), foam bath (bubble bath and the like), bath oil (bath perfume, bath capsule, and the like), milk bath, bath jelly and bath cube; cleansers; soft finishes; deodorants or aromatics; repellents; oral preparations such as dental cream, buccal wash and mouth wash; other sundry goods; and the like.

Examples of the pharmaceuticals include skin external preparations such as poultice preparations and ointments, troches, oral medicines, and the like.

The amount of the spilanthol of the present invention to be added to and blended in various foods, beverages, fragrances, cosmetics, and pharmaceuticals greatly varies depending on a target or the like, but preferably 0.00001 to 30% by mass, more preferably 0.0001 to 10% by mass, based on a normal target.

EXAMPLES

Hereinafter, the present invention will be more specifically described by way of Reference Example, Examples, and Comparative Examples, but the present invention is not to be limited thereto.

Reference Example 1

Production of N-isobutyl-3-hydroxy-6,8-decadienamide (1) Wittig Reaction Step

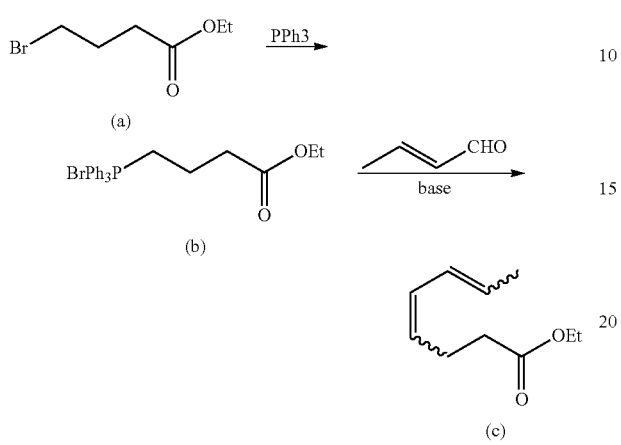

In a stream of nitrogen, ethyl 4-bromobutanoate (a) (195 g, 1.0 mol), triphenylphosphine (288 g, 1.1 mol), and acetonitrile (195 ml) were put into a 1-L flask, followed by stirring at 90° C. for 40 hours. The reaction solution was added dropwise to toluene (800 ml) and cooled to 20° C. A white solid thus precipitated was filtered, and dried under a reduced pressure (50° C./1 torr). Thus, a phosphonium salt (b) was obtained (420 g, yield 92%).

Next, in a stream of nitrogen, the phosphonium salt (b) (420 g, 0.92 mol), toluene (1600 ml), potassium carbonate (506.2 g, 3.66 mol), and crotonaldehyde (256.7 g, 3.66 mol) were put into a 5-L flask, followed by stirring at 65° C. for 7 hours. The reaction solution was cooled to room temperature, and water (840 g) was put thereinto, followed by stirring for 30 minutes, and then subjected to separation of liquid. The solvent was evaporated from the organic layer under a reduced pressure. A solid thus precipitated was removed by filtration. This solution was distilled under a reduced pressure (65 to 70° C./1.5 torr), and ethyl 4,6-octadienoate (c) was obtained (114.4 g, yield 74%).

(2) Hydrolysis Step

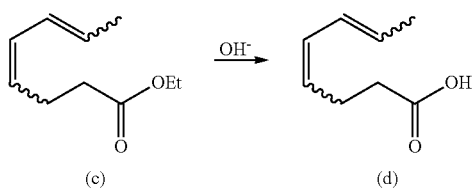

A 20% aqueous solution of potassium hydroxide (477 g, 1.7 mol) and ethyl 4,6-octadienoate (c) (114.4 g, 0.68 mol) were put into a four-neck flask, followed by stirring at 45° C. for 3 hours. The reaction solution was cooled to room temperature, heptane (230 mL) was added thereto, and 35% hydrochloric acid (177 g) was added dropwise thereto. After separation of liquid, the organic layer was washed with water (230 mL), and the solvent was evaporated therefrom under a reduced pressure. Thus, 4,6-octadienoic acid (d) was obtained (90.6 g, yield 95%).

(3) Mixed Acid Anhydride Synthesis Step

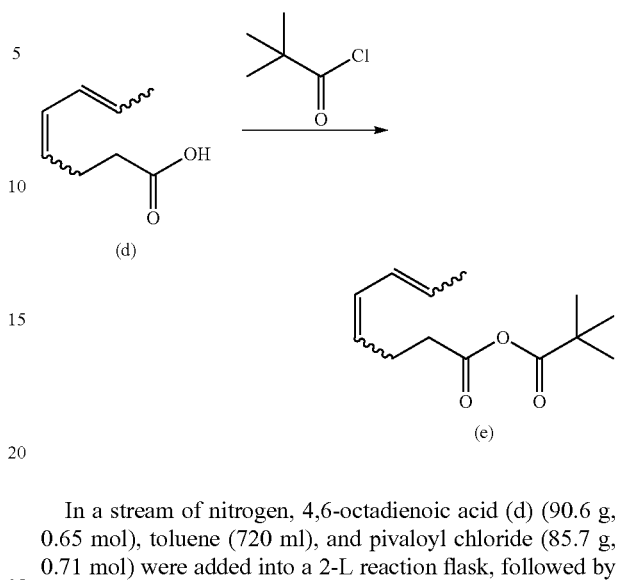

In a stream of nitrogen, 4,6-octadienoic acid (d) (90.6 g, 0.65 mol), toluene (720 ml), and pivaloyl chloride (85.7 g, 0.71 mol) were added into a 2-L reaction flask, followed by cooling at 5° C. Triethylamine (71.9 g, 0.71 mol) was added dropwise thereinto for 1 hour. Then, the temperature was gradually increased to room temperature, followed by stirring for 2 hours. After three times of washing with water (270 mL) and subsequent concentration, 139.8 g of crude pivaloyl 4,6-octadienoate acid anhydride (e) was obtained.

(4) Homologation reaction step

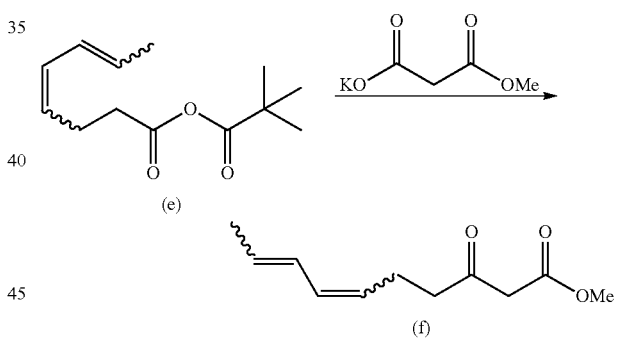

The crude pivaloyl 4,6-octadienoate acid anhydride (e) (139.8 g) obtained in (3) above, THF (140 ml), and triethylamine (69.3 g, 0.685 mol) were put into a 500-ml flask, followed by cooling to 5° C. Imidazole (45.2 g, 0.72 mol) was added thereto, followed by stirring for 1 hour.

In a stream of nitrogen, magnesium chloride (75.3 g, 0.79 mol), THF (560 ml), and a methyl malonate monopotassium salt (155 g, 0.996 mol) were put into another prepared 2-L flask. The above-described reaction solution was added dropwise thereinto for 1 hour, followed by further stirring for 5 hours. A 35% aqueous solution of hydrochloric acid (265 g, 2.55 mol) was added dropwise thereinto, followed by separation of liquid. The organic layer was washed twice with a 10% aqueous solution of sodium carbonate (660 mL). The solvent was evaporated under a reduced pressure, followed by distillation under a reduced pressure (90° C./0.5 torr). Thus, methyl 3-oxo-6,8-decadienoate (f) was obtained (88.8 g, yield 70%).

(5) Reduction Step

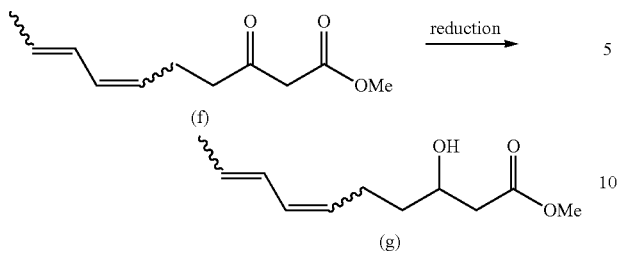

In a stream of nitrogen, sodium borohydride (5.1 g, 0.14 mol) and THF (360 ml) were put into a 1-L flask, followed by cooling to 0° C. Methyl 3-oxo-6,8-decadienoate (f) (88.8 g, 0.45 mol) was added dropwise thereinto for 1 hour. After completion of the dropwise addition, a 35% aqueous solution of hydrochloric acid (47 g) was added dropwise thereinto, followed by extraction twice with ethyl acetate (180 ml). After the organic layer was washed with water (178 mL), the solvent was removed under a reduced pressure. Thus, methyl 3-hydroxy-6,8-decadienoate (g) was obtained (86.1 g, 0.43 mol, yield 96%).

(6) Amidation Step

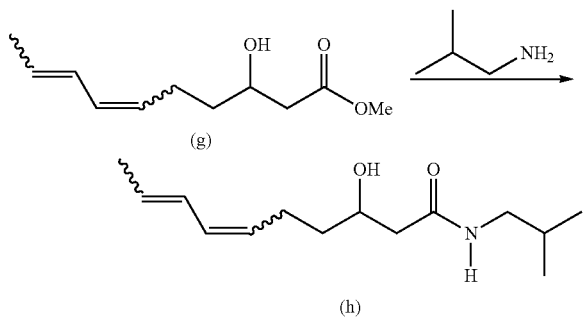

Methyl 3-hydroxy-6,8-decadienoate (g) (86.1 g, 0.43 mol) and isobutylamine (95.3 g, 1.3 mol) were put into a 500-ml flask, followed by stirring at 90° C. for 24 hours. After isobutylamine was recovered under a reduced pressure, heptane (700 ml) was added thereto, followed by cooling to 0° C. A white solid thus precipitated was filtered and dried under a reduced pressure. Thus, N-isobutyl-3-hydroxy-6,8-decadienamide (h) was obtained (85.2 g, 0.35 mol, yield 82%).

Example 1

Production of N-isobutyl-3-acetoxy-6,8-decatrienamide

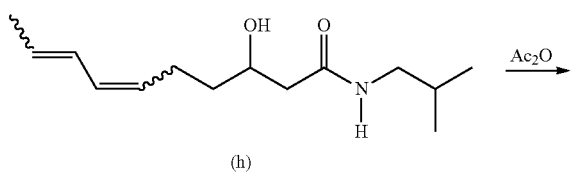

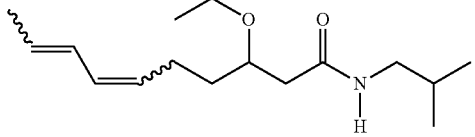

In a stream of nitrogen, N-isobutyl-3-hydroxy-6,8-decadienamide (h) (80.0 g, 0.336 mol), toluene (240 ml), triethylamine (39.65 g, 0.403 mol), and DMAP (0.21 g, 0.0017 mol) were put into a 500-ml flask. While the reaction temperature was being adjusted to 20° C., acetic anhydride (37.7 g, 0.370 mol) was added dropwise for 1 hour. After stirring for 3 hours, water (160 ml) was added thereto, and the organic layer was separated. The organic layer thus obtained was washed with a 0.5% aqueous solution of hydrochloric acid (100 ml), and washed four times with water (200 ml). The solvent was removed under a reduced pressure, and N-isobutyl-3-acetoxy-6,8-decatrienamide was obtained (93.0 g, 0.331 mol, yield 98.6%).

GC/MS (m/e); 281 (M+, 10%), 238 (4), 221 (95), 206 (12), 192 (7), 178 (5), 155 (4), 149 (13), 128 (4), 115 (73), 107 (53), 93 (60), 79 (68), 57 (100), 43 (68), 30 (21)

$^1$H-NMR (CDCl$_3$): δ 0.88 (d, 6H, J=6.7 Hz), 1.69 to 1.72 (m, 4H), 1.74 (d, 3H, J=7.2 Hz), 2.03 (s, 3H), 2.17 to 2.22 (m, 2H), 2.41 to 2.51 (m, 2H), 3.04 to 3.07 (m, 2H), 5.10 to 5.16 (m, 1H), 5.18 to 5.24 (m, 1H), 5.64 to 5.70 (m, 1H), 5.85 (br, 1H), 5.91 to 5.99 (m, 1H), 6.21 to 6.27 (m, 1H)

$^{13}$C-NMR (CDCl$_3$): δ 18.23, 20.00, 21.11, 23.44, 28.41, 33.87, 41.71, 46.83, 71.25, 126.54, 127.50, 129.43, 129.83, 131.10, 169.30, 170.56

Example 2

Production of N-isobutyl-2,6,8-decatrienamide

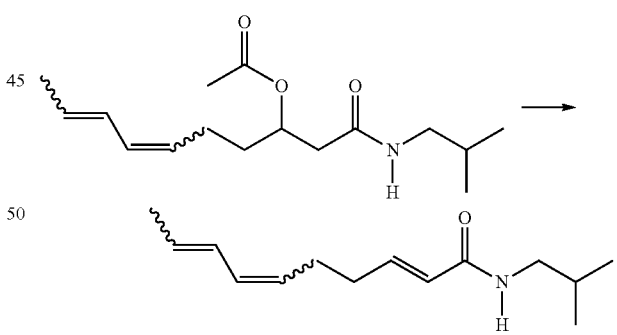

t-BuONa (35.03 g, 0.361 mol) and toluene (600 ml) were put into a 1000-ml flask, followed by cooling to −5° C. N-isobutyl-3-acetoxy-6,8-decatrienamide (93.0 g, 0.331 mol) was added dropwise thereinto for 2 hours, followed by stirring for 1 hour. Water (200 ml) was added thereto, and the organic layer was separated. Then, washing with water (186 mL) was carried out four times, and the solvent was removed under a reduced pressure. The residue was distilled under a reduced pressure (130 to 135° C./0.1 torr), and N-isobutyl-2,6,8-decatrienamide (spilanthol) (67.0 g) was obtained with a 84.0% yield.

In this connection, the purity of N-isobutyl-2,6,8-decatrienamide was 96.8%, and the isomer ratios of the alkene moiety were: 79.0% for (2E,6Z,8E), 17.5% for (2E,6E,8E), and 3.5% for (2E,6Z,8Z).

GC/MS (m/e); 221 (M$^+$, 10%), 206 (3), 192 (4), 178 (2), 167 (2), 141 (70), 126 (44), 98 (30), 81 (100), 69 (15), 53 (17), 41 (24)

$^1$H-NMR (CDCl$_3$); δ 6.82 (dt, 1H, J=15.3, 6.7 Hz), 6.28 (dd, 1H, J=10.7, 15.0 Hz), 5.97 (dd, 1H, J=10.7, 10.7 Hz), 5.87 (bs, 1H), 5.85 (d, 1H, J=15.3 Hz), 5.69 (dq, 1H, J=15.0, 6.7 Hz), 5.26 (dt, 1H, J=10.7, 6.8 Hz), 3.14 (dd, 2H, J=6.8, 6.8 Hz), 2.31 (dt, 2H, J=6.8, 6.8 Hz), 2.26 (dt, 2H, J=6.7, 6.8 Hz), 1.81 (dq, 1H, J=6.8, 6.8 Hz), 1.77 (d, 3H, J=6.7 Hz), 0.92 (d, 6H, J=6.7 Hz)

$^{13}$C-NMR (CDCl$_3$); δ 166.45, 143.74, 130.29, 129.83, 128.03, 127.09, 124.65, 47.26, 32.50, 28.97, 26.79, 20.53, 18.67

Comparative Example 1

As illustrated below, after 3-hydroxy-6,8-decadienamide (h) was converted to methanesulfonic acid ester (i), N-isobutyl-2,6,8-decatrienamide (spilanthol) was synthesized by removing the methanesulfonate moiety. The stability and sensory evaluation thereof were compared with those of N-isobutyl-2,6,8-decatrienamide (spilanthol) obtained in Example 2 above.

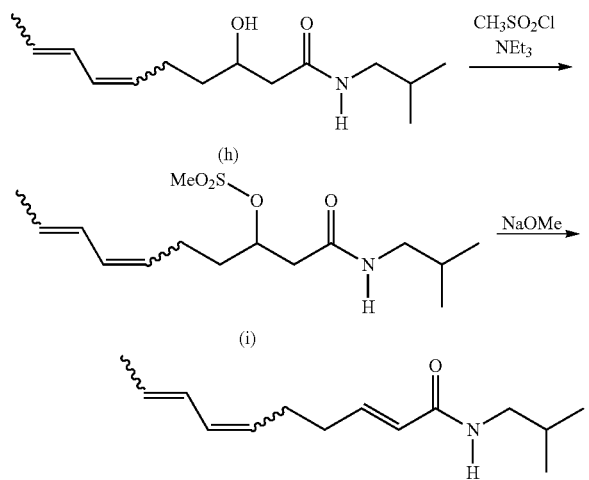

In a stream of nitrogen, N-isobutyl-3-hydroxy-6,8-decadienamide (h) (85.2 g, 0.35 mol), ethyl acetate (680 ml), and triethylamine (72.1 g, 0.70 mol) were put into a 1-L flask equipped with a stirrer, a thermometer, and a dropping funnel, followed by cooling to 5° C. Then, methanesulfonyl chloride (44.7 g, 0.392 mol) was added dropwise thereto for 1 hour. After completion of the dropwise addition, water (170 ml) was added thereto, followed by separation of liquid. Further washing with water (170 mL) was carried out three times, and the solvent was removed under a reduced pressure. Thus, N-isobutyl-3-sulfonyloxy-6,8-decadienamide (i) was obtained (108.9 g, yield 98%).

N-isobutyl-3-sulfonyloxy-6,8-decadienamide (i)

GC/MS (m/e); 317 (M+, 3%), 301 (18), 288 (2), 260 (3), 243 (1), 222 (48), 206 (12), 192 (7), 178 (5), 155 (4), 141 (18), 128 (40), 115 (50), 107 (53), 93 (63), 79 (80), 57 (100), 41 (68)

For 1 hour, a 28% sodium methoxide-methanol solution (75.5 g, 0.39 mol) was added dropwise to a solution prepared by dissolving N-isobutyl-3-sulfonyloxy-6,8-decadienamide (i) (108.9 g) in THF (425 ml) and cooling to 0° C. After completion of the dropwise addition, stirring was further carried out for 2 hours. Water (170 g) was added thereto, followed by separation of liquid. Washing with water (170 mL) was carried out twice, and the solvent was removed under a reduced pressure to obtain a crude product. This crude product was distilled under a reduced pressure (140° C./0.3 torr), and N-isobutyl-2,6,8-decatrienamide (spilanthol) (58.8 g) was obtained with a 76% yield (from N-isobutyl-3-hydroxy-6,8-decadienamide (h)).

In this connection, the purity of N-isobutyl-2,6,8-decatrienamide was 97.2%, and the isomer ratios of the alkene moiety were: 78.2% for (2E,6Z,8E), 18.0% for (2E,6E,8E), and 3.8% for (2E,6Z,8Z).

(Stability Evaluation)

The crude product of N-isobutyl-2,6,8-decatrienamide obtained in Example 2 before the distillation and the crude product obtained in Comparative Example 1 were compared as follows in terms of thermal stability at 180° C. assuming distillation at high temperature.

In a stream of nitrogen, 1 g of each of the crude products was put into a flask together with 0.1 g of hexadecane as an internal standard substance, followed by stirring at 180° C. for 6 hours. By gas chromatography, the area ratio of N-isobutyl-2,6,8-decatrienamide was compared with the area ratio of the internal standard substance to measure the remaining percentage of N-isobutyl-2,6,8-decatrienamide.

The remaining percentage after 3 hours was 98% in Example 2, and 89% in Comparative Example 1. This confirmed that N-isobutyl-2,6,8-decatrienamide produced by the production method of the present invention apparently had improved thermal stability.

(Sensory Evaluation)

The sensory evaluation was performed using aqueous solutions respectively containing 10 ppm of N-isobutyl-2,6,8-decatrienamide obtained in Example 2 and Comparative Example 1. Table 1 shows the result.

TABLE 1

| | Odor | Sensory evaluation (numbing and astringent actions) |
|---|---|---|
| Example 2 | little odor | clear and strong |
| Comparative Example 1 | unpleasant fishy odor and/or amine-like odor were smelled | strong, but slightly foreign taste |

It was confirmed that, in comparison with N-isobutyl-2,6,8-decatrienamide obtained in Comparative Example 1, N-isobutyl-2,6,8-decatrienamide obtained in Example 2 hardly had an unusual odor and exhibited excellent numbing and astringent actions.

INDUSTRIAL APPLICABILITY

The present invention provides a novel intermediate useful in manufacturing N-isobutyl-2,6,8-decatrienamide (spilanthol) useful as flavors and fragrances. The use of the intermediate enables manufacturing of high-purity spilanthol in high yield, the spilanthol being also favorable in terms of thermal stability, odor, and effectiveness.

The invention claimed is:

1. An amide ester represented by the following general formula (1):

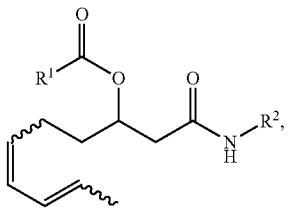

(1)

wherein $R^1$ represents an alkyl group having 1 to 6 carbon atoms; or a phenyl group which may have a substituent selected from the group consisting of alkyl groups having 1 to 4 carbon atoms, alkoxy groups having 1 to 4 carbon atoms and a halogen atom, $R^2$ represents a hydrocarbon group having 1 to 8 carbon atoms, and each wavy line represents a cis configuration, a trans configuration, or a mixture of the two configurations.

2. The amide ester according to claim 1, wherein $R^1$ is an alkyl group having 1 to 4 carbon atoms.

3. The amide ester according to claim 2, wherein $R^1$ is a methyl group.

4. The amide ester according to claim 1, wherein $R^2$ is an isobutyl group or a s-butyl group.

5. A method for producing a 2,6,8-decatrienamide, comprising
reacting the amide ester according to claim 1 with a basic compound.

* * * * *